US009949959B2

United States Patent
Armendáriz Borunda et al.

(10) Patent No.: US 9,949,959 B2
(45) Date of Patent: Apr. 24, 2018

(54) SEMI-SOLID TOPICAL COMPOSITION CONTAINING PIRFENIDONE AND MODIFIED DIALLYL DISULFIDE OXIDE (M-DDO) FOR ELIMINATING OR PREVENTING ACNE

(71) Applicant: CELL THERAPY AND TECHNOLOGY S.A. DE C.V., Mexico City (MX)

(72) Inventors: Juan Socorro Armendáriz Borunda, Mexico City (MX); José Agustín Rogelio Magaña Castro, Mexico City (MX); Pedro Peña Santoyo, Mexico City (MX); Laura Vázquez Cervantes, Mexico City (MX)

(73) Assignee: CELL THERAPY AND TECHNOLOGY S.A. DE C.V., Mexico City (MX)

( * ) Notice: Subject to any disclaimer, the term of this patent is extended or adjusted under 35 U.S.C. 154(b) by 0 days.

(21) Appl. No.: 15/098,970

(22) Filed: Apr. 14, 2016

(65) Prior Publication Data

US 2016/0228424 A1 Aug. 11, 2016

Related U.S. Application Data

(63) Continuation of application No. 14/388,447, filed as application No. PCT/MX2013/000027 on Feb. 27, 2013, now abandoned.

(30) Foreign Application Priority Data

Mar. 28, 2012 (MX) .................... MX/a/2012/003694

(51) Int. Cl.
| | |
|---|---|
| A61K 31/4412 | (2006.01) |
| A61K 31/351 | (2006.01) |
| A61K 9/00 | (2006.01) |
| A61K 9/06 | (2006.01) |
| A61K 31/4418 | (2006.01) |

(52) U.S. Cl.
CPC ........ *A61K 31/4412* (2013.01); *A61K 9/0014* (2013.01); *A61K 9/06* (2013.01); *A61K 31/351* (2013.01); *A61K 31/4418* (2013.01)

(58) Field of Classification Search
CPC ................ A61K 9/0014; A61K 31/351; A61K 31/4418; A61K 9/06; A61K 31/4412; A61K 2300/00
See application file for complete search history.

(56) References Cited

U.S. PATENT DOCUMENTS

| | | | |
|---|---|---|---|
| 4,105,782 A | 8/1978 | Yu et al. | |
| 4,376,118 A | 3/1983 | Daher et al. | |
| 5,009,895 A | 4/1991 | Lui | |
| 5,811,130 A | 9/1998 | Boettner et al. | |
| 5,958,420 A | 9/1999 | Jenson | |
| 6,365,131 B1 | 4/2002 | Doshi et al. | |
| 7,109,246 B1 | 9/2006 | Hawtin | |
| 8,492,412 B2 | 7/2013 | Magana Castro et al. | |
| 9,408,836 B2 | 8/2016 | Armendariz Borunda et al. | |
| 2004/0029946 A1 | 2/2004 | Arora et al. | |
| 2004/0235946 A1* | 11/2004 | Ott ....................... A61K 31/255 514/517 |
| 2006/0051339 A1 | 3/2006 | Sivak | |
| 2006/0115503 A1 | 6/2006 | Goyal | |
| 2008/0319026 A1 | 12/2008 | Gant et al. | |
| 2011/0224265 A1* | 9/2011 | Magana Castro ... A61K 9/0014 514/345 |
| 2013/0245073 A1 | 9/2013 | Magana Castro et al. | |
| 2014/0296300 A1 | 10/2014 | Armendariz Borunda et al. | |
| 2015/0148382 A1 | 5/2015 | Armendariz Borunda et al. | |
| 2015/0231098 A1 | 8/2015 | Magana Castro et al. | |
| 2016/0287567 A1 | 10/2016 | Armend Riz Borunda et al. | |
| 2017/0216268 A1 | 8/2017 | Magana Castro et al. | |

FOREIGN PATENT DOCUMENTS

| | | |
|---|---|---|
| CN | 101972236 | 2/2011 |
| EP | 1356816 A1 | 10/2003 |
| EP | 2177220 A1 | 4/2010 |
| MX | 2013008151 A | 10/2013 |
| WO | 2000/16775 A1 | 3/2000 |

(Continued)

OTHER PUBLICATIONS

Allicinnow, "allicin," retrieved online at: http://www.allicinnow.com/allicin/acne-treatment/, 2 pages (2010).
Armendariz-Borunda, Juan et al., "A Controlled Clinical Trial With Pirfenidone in the Treatment of Pathological Skin Scarring Caused by Burns in Pediatric Patients," Annals of Plastic Surgery, vol. 68(1):22-28 (2012).
International Preliminary Report on Patentability for Application No. PCT/MX2008/000107, 5 pages, dated Dec. 1, 2009.
International Preliminary Report on Patentability for Application No. PCT/MX2012/000067, 8 pages, dated Aug. 7, 2013.
International Search Report and Written Opinion for Application No. PCT/MX2012/000067, 12 pages, dated Nov. 22, 2012.
International Search Report and Written Opinion for Application No. PCT/MX2013/000027, 11 pages, dated Jun. 5, 2013.

(Continued)

*Primary Examiner* — Anoop K Singh
*Assistant Examiner* — Doan T Phan
(74) *Attorney, Agent, or Firm* — Nelson Mullins Riley & Scarborough LLP; Jill Gorny Sloper, Esq.; Cynthia L. Kanik

(57) ABSTRACT

The instant invention relates to a semi-solid topical composition containing Pirfenidone and an antimicrobial/antiseptic agent such as Modified Diallyl Disulfide Oxide (M-DDO) and its preparation process, offering advantages compared to other pharmaceutical forms of topical administration known in the state of the art, useful as antifibrotic, anti-inflammatory and antiseptic agent in the prevention, treatment and reversion of acne and post acne lesions. Said compositions is also useful for reducing skin redness, detaining the formation of new acne outbreaks, reversing already existing outbreaks and regenerating skin damage caused by acne.

9 Claims, 15 Drawing Sheets

(56) References Cited

FOREIGN PATENT DOCUMENTS

| WO | 0016775 A1 | 3/2000 |
|---|---|---|
| WO | 2004/073713 A1 | 9/2004 |
| WO | 2007/038315 A2 | 4/2007 |
| WO | 2008107873 A1 | 9/2008 |
| WO | 2009/022899 A1 | 2/2009 |
| WO | 2013/012307 A1 | 1/2013 |
| WO | 2013/147577 A1 | 10/2013 |

OTHER PUBLICATIONS

International Search Report for Application No. PCT/MX2008/000107, 3 pages, dated Dec. 9, 2008.
Josling, Peter, "Peter Josling's PowerPoint on AllicinCenter Products and Their Uses," retrieved from the internet at: http://allicincenter.com/reference.php?id=products, 15 pages (2013).
U.S. Appl. No. 14/421,616, filed Feb. 23, 2015, José Augustín Rogelio Magaña Castro.
U.S. Appl. No. 15/435,494, Sep. 8, 2017.
U.S. Appl. No. 15/177,760, Apr. 17, 2017.
U.S. Appl. No. 14/421,616, Mar. 6, 2017.
U.S. Appl. No. 14/421,616, May 19, 2016.
U.S. Appl. No. 14/421,616, Nov. 9, 2015.
Gad, C.G., "Pharmaceutical Manufacturing Handbook: production and processes," John Wiley & Sons, ISBN: 978-0-470-25958-0, 1386 pages (Mar. 2008).
International Preliminary Report on Patentability, PCT/MX2013/000099, dated Dec. 19, 2014, 7 pages.
International Search Report and Written Opinion, PCT/MX2013/000099, dated Aug. 8, 2014, 3 pages.
Tiwari, S., et al., "Applications of Complementary Polymers in HPMC Hydrophilic Extended Release Matrices," Drug Delivery Technology, Formulating Hydrophilic Matrix Systems, vol. 9(7), 7 pages (2009).

* cited by examiner

[M-DDO]

{[1,2-diallyl-1-(5-methyl-tetrahydro-2H-pyran-2-yloxy)disulfonium] + 6-[(benzyl, methyl, octylammonium) (hydroxymethylamin)(methylamin)]-tetrahydro-2H-pyran-3-oxy]}

Beginning      After 26 weeks

Beginning      After 26 weeks

Before Treatment  After 26 weeks

Before Treatment      After 4 weeks

Before 8 weeks after

Before          4 weeks after

Before treatment 72 weeks after

Before treatment        72 weeks after

Before treatment 72 weeks after

Start      20 weeks after

SEMI-SOLID TOPICAL COMPOSITION CONTAINING PIRFENIDONE AND MODIFIED DIALLYL DISULFIDE OXIDE (M-DDO) FOR ELIMINATING OR PREVENTING ACNE

RELATED APPLICATIONS

This application is a continuation of U.S. patent application Ser. No. 14/388,447, filed Feb. 5, 2015, which is a 35 U.S.C. 371 national stage filing of International Application No. PCT/MX2013/000027, filed on Feb. 27, 2013, which claims priority to Mexican Patent Application No. MX/A/2012/003694, filed on Mar. 28, 2012. The contents of the aforementioned applications are hereby incorporated by reference in their entireties.

FIELD OF THE INVENTION

The invention relates to a semi-solid topical composition containing 8% Pirfenidone and 0.016% Modified Diallyl Disulfide Oxide (M-DDO) acting synergically for eliminating or preventing the occurrence of various forms of skin acne and as antimicrobial and antiseptic agent.

BACKGROUND OF THE INVENTION

Acne is an inflammatory disease of the pilosebaceous follicles associated to alterations of keratinization and seborrhea; it is characterized by the formation of skin lesions such as comedones, papules, pustules, cysts, and abscesses, frequently leaving residual scars.

The acne is doubtless the most frequent skin disease worldwide; it has traditionally been considered that two main factors are involved in acne occurrence, the exaggerated production of sebum and abnormal desquamation of epidermal cells finally causing an excessive keratinization, but recent studies have added genetic predisposition and inflammation as acne-causing factors. According to recent statistical data, it is estimated that about 85% of people between 11 and 30 years of age suffer from acne, i.e. about 20 million people are affected in Mexico alone. The incidence data show a maximum peak at the age of 18, followed by a progressive reduction which is more prominent after the age of 30; however, between 25 and 35% of adults older than 35 years of age show occasional acne exacerbations.

Because many factors are involved, the cause of acne is not precisely known. However the genetic background combined with endocrine, inflammatory and infectious factors are the ones involved in the polymorphic characteristics of acne.

Five main primary pathogenic factors interact in a complex way to cause acne lesions, i.e.:
1. Genetic predisposition.
2. Excessive production of sebum by the sebaceous glands.
3. Alterations of the keratinization process with abnormal desquamation of the sebaceous follicular epithelium (causing comedogenesis).
4. Proliferation of *Propionibacterium acnes*.
5. Release of skin inflammatory mediators, namely TNF-alpha and IL-1 alpha.

Genetic Factors

The genetic predisposition is not mediated through a simple Mendelian character, but is caused by a polygenic mechanism originating from the special receptivity of the pilosebaceous follicle to respond more intensively to androgens, in a fashion different from the way healthy people respond. This phenomenon is possibly caused by a major activity and concentration of the 5-alpha-reductase present in the sebaceous glands. In patients with acne, it is frequent to find a family background with this entity, even the same clinical type and same identity.

Sebum Production Factor

Several studies conducted regarding sebum function in acne, have shown that the sebaceous lipids are regulated by peroxisome proliferation activated-receptors (PPAR) and by sterol transcription factors.

The PPAR nuclear receptors act together with retinoids X receptors (RXR), to regulate epidermis growth and differentiation as well as lipids metabolism. Sterol transcription factors regulate the increase in the formation of sebaceous lipids induced by the insulin-like growth factor (IGF-1).

Other researches regarding the function of the sebaceous gland have contributed to offer information about the essential function of these glands in skin functions regulation. The sebaceous gland has direct and indirect antibacterial activities. Sapienic acid, a sebum lipid, has an innate antimicrobial activity and is increased by the activation of Toll-like receptor 2 (TLR-2) through contact with skin bacteria. Moreover, the sebaceous gland produces antibacterial peptides and pro-inflammatory cytokines that are induced in the sebocytes due to the presence of bacteria.

The sebaceous gland acts as an endocrine organ that responds to androgen and hormone changes and is the control center for a complex program regulating neuropeptides that act as the hypothalamus-hypophysis-adrenal axis. This function of the sebaceous gland is influenced mainly by the corticotropin-releasing hormone, the protein binding to it, and by the corticotropin receptors. The corticotrophin-releasing hormone levels change in response to stress and its function as regulator of the sebaceous gland is to act as a brain-skin connection explaining the relationship between stress and skin inflammatory disorders, especially atopic dermatitis and acne. Moreover, it has been reported that ectopeptidase receptors such as dipeptidyl peptidase IV and aminopeptidase-N play an important part in the regulation of sebocytes.

Other researchers have shown, in a cell line derived from human keratinocytes, that sebum lipid peroxidation can activate inflammatory mediators, including interleukin-6 (IL-6) and lipoxygenase. The oxidized squalene can also stimulate keratinocytes proliferation behavior, suggesting that this lipid could be partially responsible for comedone formation. It has also been shown that lipoperoxides have a proinflammatory effect on the sebaceous follicle. Lipoperoxides produce leukotriene 4, a powerful chemoattractant recruiting neutrophils and macrophages and stimulating the production of pro-inflammatory cytokines.

Endocrine Factors

Androgens are hormones synthesized in the testicles, ovaries and suprarenal cortex. During puberty, through mechanisms which are little known, the hypophysis starts secreting larger quantities of luteinizing hormones (LH) and follicle-stimulating hormones (FSH) that, together, are responsible for increasing testicular growth, spermatogenesis and steroidogenesis. Testosterone acts on the sebaceous glands, increasing their size and sebum synthesis. In women, the mechanism is similar, and the luteinizing hormone acts on the ovaries increasing testosterone synthesis and secretion.

Through skin biopsies of the face of patients with acne, it has been observed that sebaceous glands are larger and more lobulated during puberty, precisely the stage during which there is an increase in the levels of the mentioned hormones.

The conclusion is that acne is induced by androgens, but only because of a genetic predisposition that causes alteration in androgens normal metabolism at pilosebaceous follicle level, with an increase in the concentration and activity of 5-alpha-reductase, present in the sebaceous glands of the affected parts.

Infectious Factors

In the past, it was believed that acne was only an infectious process caused by the bacteria "*Acne bacillus*". Then the function of bacteria in acne pathogenesis was questioned after said organism, now called *Propionibacterium acnes* was isolated from control subject not affected by acne.

There is little qualitative difference between acne patients and acne-free control patients when microbiological studies are conducted. The skin flora in both groups is essentially a triad including *Propionibacterium acnes*, and *Staphylococcus epidermis* and a yeast that can be *Pityrosporum ovale* or *Pityrosporum orbiculare*.

Despite the above, the possible association between bacteria and acne pathogenesis was reinforced because of well documented findings of clinical improvement in acne patients treated with systemic antibiotics. The antibacterial therapy does not affect *P. orbiculare* or *P. ovale* because they are on the upper part of the acrofundibulum of the sebaceous follicle. The anaerobic *P. acnes*, on the other hand, appear to play a central part in the development of inflammation in acne. Maybe the most convincing evidence is the demonstration that the antibiotic therapy leads to a significant suppression of *P. acnes* which is accompanied by a reduction in the number of inflammatory lesions.

*Propionibacterium acnes* and *Staphylococcus epidermis* produce a lipase that hydrolyzes serum triglycerides in free fatty acids that are powerful irritating agents of the follicular canal, when they are applied to the skin or injected intradermally, causing inflammation and comedones.

It has also to be stated that *Propionibacterium acnes* activates the complement system alternatively, and this has led to postulate that this infectious mechanism could play an important part in the production of acne inflammatory lesions.

Keratinization Factor

During puberty, in response to the larger quantities of androgens produced at this stage, the sebaceous glands that were previously relatively inactive increase in size and become more lobulated, augmenting sebum production that is poured outside; this explains the first acne sign: seborrhea.

The recently synthesized sebum contains triglycerides, squalene and wax esters and it is known that *Propionibacterium acnes* and *Staphylococcus epidermis* through a lipase hydrolyze the triglycerides of this sebaceous material, converting them into free fatty acids that together with other irritating substances such as squalene and oleic acid, cause an inflammation of the follicular canal that, in turn, responds to the inflammation with hyperkeratosis. The resulting corneal material falls into the follicle lumen forming, together with the excessive sebum, a plug that distends the follicle walls. This follicle, unable to excrete the material, produces further inflammation, causing the first and most important acne elemental lesion: comedone, provoking the dilatation of the follicular hole through the pressure exerted by the plug in its attempt to be expulsed.

Inflammatory Factors

Several studies have focused on the function of inflammatory mediators, as well as on the interrelation of these factors with sebaceous lipids and matrix metalloproteinases (MMP's) in acne physiopathology.

One of the pioneer researches in this field was carried out by Jeremy et al in 2003 who studied the initial events of acne lesions and found that the immunological changes and inflammatory responses occur before keratinocytes hyperproliferations with a pattern similar to a delayed type IV hypersensitivity response.

The immune response is mediated through CD4+ lymphocytes and macrophages. These researchers propose as explanation that the subsequent production of cytokines activates local endothelial cells and induces an exacerbated regulation of inflammatory vascular markers (E-selectin, vascular cell adhesion molecule-1 [VCAM-1], intracellular adhesion molecule 1 [ICAM-1], and the human leukocyte antigen DR [HLA-DR]) in the vasculature around the pilosebaceous follicle.

An important fact is that all the process is initiated by the exacerbated regulation of IL1-$\beta$ that has a proinflammatory action in response to the relative deficiency of linoleic acid caused by the excess of sebum and the perturbation of the barrier function within the follicle.

More than a decade ago, in an in vitro study, Vowels et al demonstrated the presence of a soluble factor of *P. acnes* that also induces the production of proinflammatory cytokines in cellular lines derived from human monocytes. This product of *P. acnes* induces the synthesis of the Tumor Necrosis Factor alpha (TNF-$\alpha$) and interleukin 1-beta (IL1-$\beta$) in said cellular lines. It was also shown that cytokines induction by *P. acnes* occurred through the activation of "TOLL-LIKE-2" (TLR-2) receptor that triggers said inflammatory responses. Said transmembrane protein has a cytoplasmic portion homologous to the interleukin 1 (IL-1) receptor, and can thus trigger the signaling cascade activating the nuclear transcriptional factor Kappa-B (NF-k$\beta$).

NF-k$\beta$ is a key transcription factor regulating the transcription of genes codifying for the production of proinflammatory proteins such as TNF-$\alpha$, Interleukin 1 (IL-1) and Interleukin-6 (IL-6).

The activation of other transcriptional factors, AP-1 (Activator Protein-1) induces MMP's genes, the proteic products of which degrade and alter the dermal matrix.

Other recent studies have shown that this chain of events occurs in inflammatory lesions of patients with facial acne. It has been shown that *Propionibacterium acnes* also induces Toll-type receptors. This is additional evidence that the inflammatory cytokines acting through autocrine and paracrine mechanisms amplify their corresponding receptors and amplify the signaling route activating the Activator Protein 1 (AP-1) that is a transcription factor.

Further, it has been shown that the liberation of the same transduction signals does not only stimulate proinflammatory cytokines but also stimulates enzymes production in the fibroblast, said enzymes denominated MP's are the proteins responsible for extracellular matrix degradation, causing imperfect repair of the chronic inflammatory acne lesions and finally leading to skin sequelae that manifest themselves as filling defects commonly known as "ice-picks lesions" or "pockmarks". FIG. 2 shows the molecular chain for the production of said dermal sequelae.

In FIG. 3, the transmission system, at cellular level, of signals intervening in acne and finally triggering the inflammatory process in which Toll-type receptors intervene to activate the nuclear factor NF-k$\beta$ that causes the production of TNF-$\alpha$, IL-1, IL-6 and other proinflammatory cytokines is shown. Thus, also through this type of receptors, AP-1 is activated, which is a transcription factor that will finally activate MMP's, enzymes involved in the formation of post-acne scars and deficiencies in the production of extracellular matrix. In acne treatment, the use of antimicrobial agents is usual among physicians, because clinically there is an improvement in acne patients when this type of products is used, due to the potentiating factor of *P. acnes* in the metabolism of sebum causing an irritating effect that will generate further inflammation in the patient.

The combination of two elements, Pirfenidone and M-DDO, the final objective of which is the symptomatological management of acne and its sequelae, has shown to be highly effective in the treatment of acne patients at different lesion stages, from light to severe, showing an improvement with regard to severity, number and duration of lesions, that are the main objectives for the acne physician.

In short, it can be said that acne shows a complex interaction of many factors creating a complex problem where some key points are confluent with genetic factors and inflammation, such as:
1. Inflammatory events precede hyper keratinization.
2. *P. acnes* contributes to the inflammation through the activation of Toll-like receptors in the inflammatory cell membranes.
3. Sebum production is partially regulated by PPAR receptors.
4. The sebaceous gland is a neuroendocrine-inflammatory organ that coordinates and executes a local response to the stress and to normal functions.
5. Androgenes influence follicular cells.
6. Oxided lipids in sebum can stimulate the production of inflammatory mediators.
7. Matrix metalloproteinases (MMP's) are present in sebum and their number diminishes as the lesions are treated.

Objective of the Invention

The main objective of the instant invention is to offer semi-solid topical compositions for eliminating, reducing or preventing the occurrence of skin acne, comprising preferably a composition of 8% in weight of pirfenidone [1-phenyl-5-methyl-2-(1H)-pyridone] and M-DDO at a concentration of 0.016%, a gelling agent and one or more excipients or additives.

Another object of the instant invention is the use of M-DDO as antimicrobial and antiseptic agent eliminating the need for using other preservative agents in the composition. Moreover, the objective of the instant invention is a treatment method and/or the application or pharmaceutical use of a semisolid topical composition containing pirfenidone and M-DDO for eliminating, reducing or preventing acne. Moreover, said semi-solid topical composition acts to prevent chronic inflammation caused by acne, reduces skin redness, detains the formation of new acne outbreaks, reverts the already existing outbreaks, regenerates acne-related skin damage and prevents and removes post-acne scars.

Other objectives of the instant invention relate to the pharmaceutical presentation of the topical composition in gel, cream or ointment form.

An additional objective is the manufacturing process of the semi-solid topical composition containing pirfenidone and M-DDO for eliminating, reducing or preventing acne. The above objectives illustrate the instant invention but do not limit it; besides, its applications and/or pharmaceutical uses are shown in the preparation of drugs for eliminating, reducing or preventing acne.

BRIEF DESCRIPTION OF THE FIGURES

Other characteristics and advantages of the instant invention shall be obvious from the following detailed description of the objects and preferred embodiments, of the attached claims and of the drawings and figures accompanying them, wherein:

DETAILED DESCRIPTION OF THE INVENTION

Figure 1:
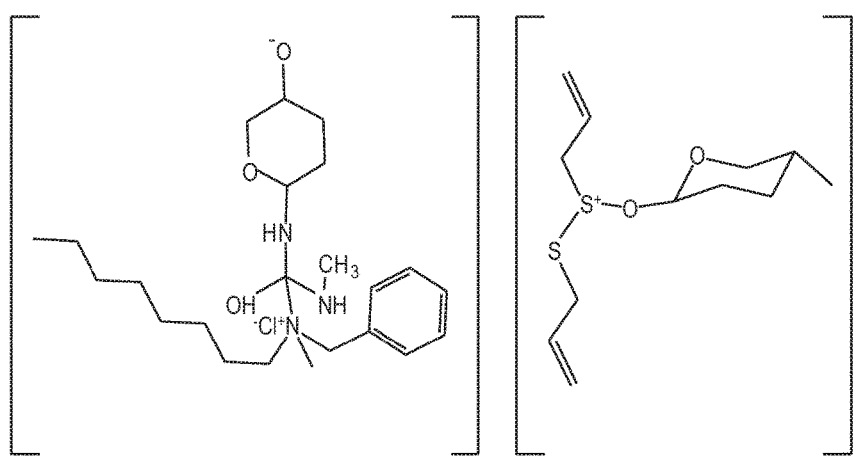
FIG. 1 shows M-DDO chemical formula.
Figure 2:
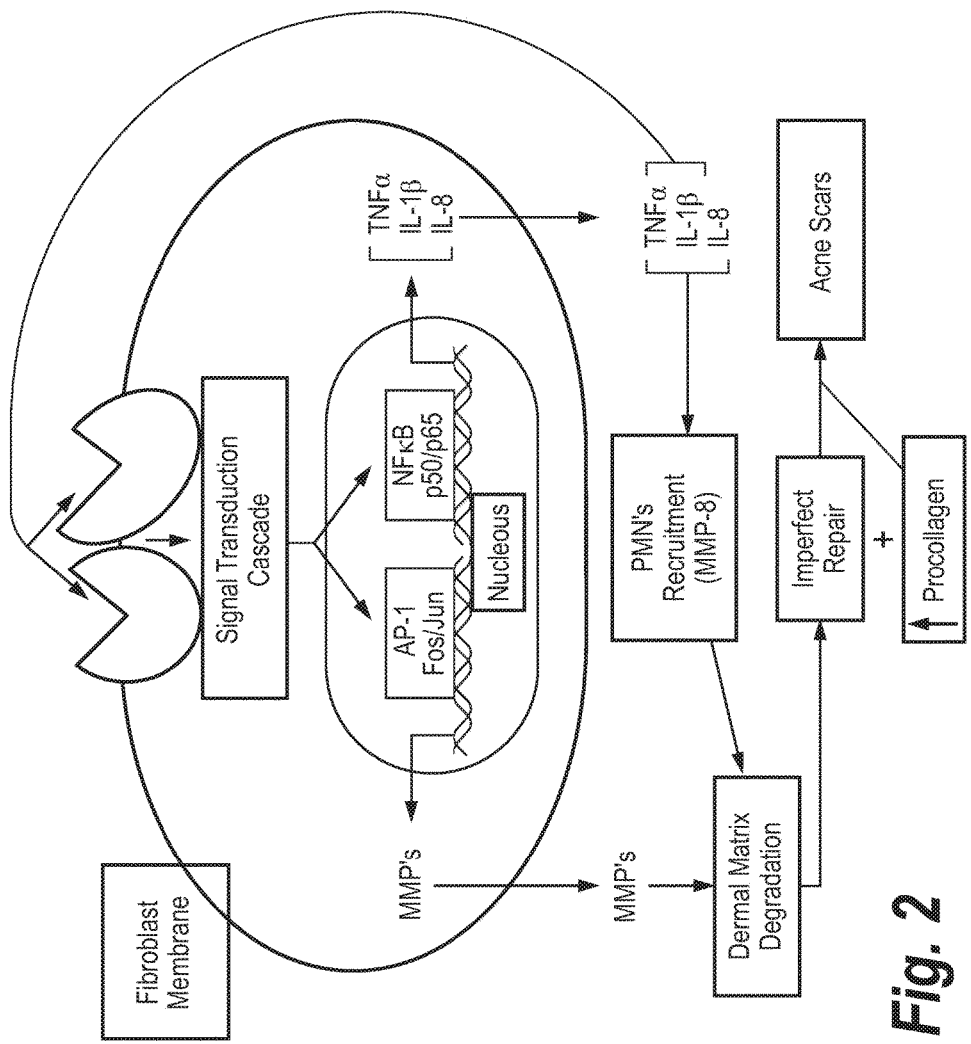
FIG. 2 shows the molecular chain of dermal sequelae.

The instant invention relates to a semi-solid topical composition in the form of a gel, cream or ointment comprising [1-phenyl-5-methyl-2-(1H)-pyridone] preferably at 8%, a gelling agent, cellulose derivatives, polyacrylic reticulated acid polymers and carboxyvinylic derivatives; and other additives such as triethanolamine as neutralizing agent, propylene glycol as solubilizer, macrogol-glycerol hydroxystearate as non-ionic solubilizer, among other commonly used additives in gel preparation. Moreover, the semi-solid topical composition contains 0.016% weight/volume of an antimicrobial and antiseptic agent such as M-DDO. [1-phenyl-5-methyl-2-(1H)-pyridone) is a drug that has been used in the restoration of tissues showing fibrotic lesions and for preventing fibrotic lesions. This compound, called Pirfenidone, is per se a known compound and its pharmacological effects have been described, for example, in Japanese applications KOKAI numbers 87677/1974 and 1284338/1976, as anti-inflammatory agent having antipyretic and analgesic effects. U.S. Pat. No. 3,839,346, published on Oct. 1, 1974, U.S. Pat. No. 3,974,281, published on Aug. 10, 1978, U.S. Pat. No. 4,042,699, published Aug. 16, 1977, and U.S. Pat. No. 4,052,509, published on Oct. 4, 1977, describe methods for obtaining pirfenidone, as well as its use as anti-inflammatory agent. Mexican patent 182,266 describes the antifibrotic activity of Pirfenidone [1-phenyl-5-methyl-2-(1H)-pyridone].

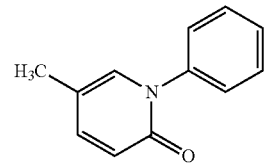

$C_{12}H_{11}ON$
MW=185
Name: 1-phenyl-5-methyl-2-(1H)-pyridone.

The combination of Pirfenidone and M-DDO generates a semi-solid composition for swift prevention, control and elimination of skin problems caused by acne. It acts as anti-inflammatory and antimicrobial agent due to its dual action mechanism, because, besides blocking pro-inflammatory cytokines—especially TNF-α (Tumor Necrosis Factor-alpha)—, it also shows antimicrobial and antiseptic action. It thus acts on two of the main causes of acne.

Thus, the semi-solid topical composition of Pirfenidone and M-DDO:
Has a direct effect blocking TNF-α, TGF-β and other proinflammatory cytokines;

Through its MMP's modulating action, it helps prevent scar sequelae;

It has an effect on KGF, modulating keratinocytes production;

It has a potent anti oxidant effect, helping the metabolism of sebaceous gland and blocking the inflammatory stimulation of *P. acnes*.

Upon reducing the inflammation it opens gland ducts and thus inhibits anaerobic bacterial growth.

Moreover, the results shown in FIGS. 4 to 15 clearly evidence that patients with acne outbreak respond excellently to the treatment with the semi-solid topical composition object of the instant invention when it is applied two or three times a day. In most of the patients, obvious improvements are obtained in less than a month, when it is applied on a daily basis. The series of FIGS. 4-15 clearly show the potent action of Pirfenidone and M-DDO on acne and the sequelae caused by said disease.

The semi-solid topical composition acts as a biomodulator of the serum concentrations of inflammatory proteins and thus has an anti-TNF-alpha and anti IL-6 action, and acts directly on acne inflammatory factor; moreover, through its antimicrobial effect, it acts on the bacteria *Propionibacterium acnes*.

The semi-solid topical composition permits that the pharmacological properties of pirfenidone and M-DDO acts synergically on the skin, and thus the selection of a gelling agent is extremely important. The gelling agents were thus selected from the group consisting of: methylcellulose, hydroxypropylcellulose, sodium carboxymethylcellulose, polyvinyl alcohol, polyvinylpirrolidone, carboxyvinyl polymer, carbomer, acrylic polymers. Said gelling agents are used together with additives for obtaining a pH ranging from 5 to 6.4, at which level said gelling agents show a higher viscosity. Said composition also comprises M-DDO, propylene glycol, macrogol-glycerol hydroxystearate and triethanolamine.

Thus, the semi-solid topical composition of the instant invention reduces or prevents skin acne and comprises preferably 8% in weight of the composition of Pirfenidone and 85 to 95% in weight of the composition of a gelling agent selected from the group consisting of methylcellulose, hydroxypropylcellulose, sodium carboxymethylcellulose, polyvinyl alcohol, polyvinylpirrolidone, carboxyvinyl polymers, carbomer, acrylic polymers; and one or several additives selected from propylene glycol, macrogol, glycerol, hydroxystearate, besides M-DDO.

Thus, the semi-solid topical composition is also effective for preventing chronic inflammation caused by acne, for reducing skin redness, for detaining the formation of new acne outbreaks, for reverting the already existing outbreaks, for regenerating skin damage caused by acne and for preventing and removing past acne scars.

Preparation Process

The semi-solid topical composition containing Pirfenidone and M-DDO is prepared following a process comprising the following stages:

1.—In a container, place 90% of the total water and add:

Carbomer (1 g)

Leave till complete moisturizing. (IDENTIFY MIXTURE "A")

2.—In another container, place and heat at 40° C. (IDENTIFY SOLUTION "A")

Propylene glycol (50 g)

Add slowly, under constant stirring till complete dissolution, maintaining at 40° C.

1-phenyl-5-methyl-2-(1H)-pyridone (8 g)

Add slowly and under constant stirring, maintaining at 40° C.

Macrogol-glycerol Hydroxystearate (13 g)

Add under constant stirring, maintaining at 40° C.

Modified Diallyl Disulfide Oxide (M-DDO) (0.8 g)

3.—In another container, place 10% of the total water and under constant stirring add:

Triethanolamine (1 g)

Stir till homogenization (IDENTIFY SOLUTION "B")

4.—Add to the container (step 1), one by one, under constant stirring till homogenization each time and in the indicated order.

SOLUTION "A"

SOLUTION "B"

5.—Sample and analyze the topical composition.

Pirfenidone and M-DDO Composition

The composition of 0.016% Pirfenidone and M-DDO described in the instant invention permits the obtainment of a gel, cream or ointment containing contact antimicrobial/antiseptic agent, that are stable, biodegradable, and non-toxic having a wide action spectrum not only against gram negative and gram positive microorganisms but also against fungi.

FIG. 1 shows the formula of Modified Diallyl Disulfide Dioxide [M-DDO], the chemical name of which is [1,2-diallyl-1-(5-methyl-tetrahydro-2H-pyran-2-yloxy)disulfonium]+6-[(benzyl, methyl, octylammonium) (hydroxymethylamin)(methylamin)]-tetrahydro-2H-pyran-3-oxy] chloride:

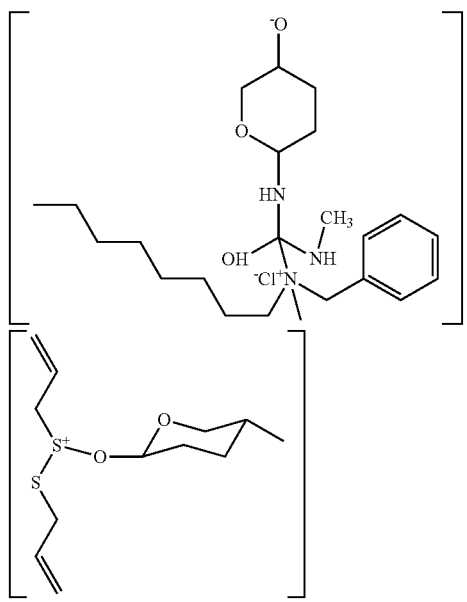

{[1,2-diallyl-1-(5-methyl-tetrahydro-2H-pyran-2-yloxy)disulfonium]+6-[(benzyl, methyl, octylammonium) (hydroxymethylamin)(methylamin)]-tetrahydro-2H-pyran-3-oxy]}

$C_{35}H_{62}O_5N_3S_2Cl$

Molecular weight=703.5

Tables 1, 2, 3 and 4 (shown hereinafter) present the information obtained after conducting microbiological tests, also known as antimicrobial challenge, of M-DDO against various bacteria, showing its powerful anti-bacterial capacity. Moreover, Table 5 (shown hereinafter) presents the results of M-DDO against *Propionibacterium acnes*. Moreover, said table also shows that the combination of Pirfenidone and M-DDO (semi-solid topical composition containing Pirfenidone and M-DDO) results in a highly effective removal of *P. acnes* in a matter of seconds.

[Pirfenidone and ODD-M] contains Modified Diallyl Disulfide Oxide (M-DDO), this active substance has been identified, before its chemical modification as Allicin, substance coming from a plant the scientific name of which is *Allium sativum*, having the original formula:

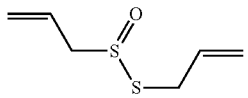

$C_6H_{10}OS_2$
Molecular Weight=162
Name: Diallyl-Disulfide Oxide

The use of natural substances in the treatment of various diseases—including diseases of infectious etiology—constitutes currently a challenge for modern medicine. In 1994, Cavallito et al. isolated and identified the active compound of *Allium sativum* extracts which they denominated Allicin and in 1947 they synthesized Diallyl Disulfide Oxide (Allicin) but unfortunately could not prepare a stable molecule from it because of its continuous loss of efficacy in a very short period of time. Between 2000 and 2005, a group of Mexican researchers could stabilize diallyl Disulfide oxide, adding a cofactor that does not modify the allicin antimicrobial action or other actions but grants it a long term action, obtaining thus a stable, biodegradable, non-toxic and large spectrum action contact antimicrobial/antiseptic agent, not only against gram negative and gram positive microorganisms but also against fungi. The following antimicrobial action mechanisms of M-DDO in this topical composition [Pirfenidone and M-DDO] have been proposed:
 1. Various chemical reactions of M-DDO sulphydric radicals on microbial metabolism, causing mainly the enzymatic inhibition of 11 enzymes of the microorganism either inserting sulfur radicals or causing protein modifications in the enzymes, and inhibiting thus metabolic actions of the microorganism, causing its death.
 2. The creation of free radicals (ROS), through Redox reactions, that break the microorganism cell wall through oxidative stress, upon "sequestering" the oxygen serving as union between the chains of NAG (n-Acetyl-glucosamine acid) and NAM (N-Acetyl muramic acid), weakening the microorganism wall, causing its rupture and thus the death of the microorganism.
 3. The inhibition of the microorganism protein unfolding, through the inhibition of the RNA polymerase enzyme, which is a sulfur-dependent enzyme.
 4. Metal metabolism alteration in the microorganism, causing also metabolic alterations in said microorganism.

Antimicrobial Challenges

Various antimicrobial challenges have been studied in various institutions in order to evaluate the efficacy of M-DDO [Pirfenidone and M-DDO] against the most frequent microorganisms susceptible to develop resistance and against some microorganisms that may cause grater problem with regard to their eradication because of spore production.

The initial challenges are conducted with collection microorganisms universally requested for evidencing the efficacy of a product. The challenges performed in our laboratory show that with a 30 second contact, more than 100.00% of the microorganisms were eliminated, including *Candida albicans*. Studies conducted at the Universidad Nacional Autónoma de México resulted in a 99.999% elimination of the microbial charge. Moreover, results of studies conducted by a company authorized by the authorities to perform challenge studies show results that are similar to the results obtained in the test conducted at UNAM, UAEM and in our laboratory (Grupo Medifarma) (Tables 1, 2 and 3).

TABLE 1

Microbial challenge studies conducted at Grupo Medifarma

| TEST MICROORGANISM | CONTACT TIME 30 seconds |
|---|---|
| *Escherichia coli* ATCC 10536 | 100% |
| *Escherichia coli* ATCC 11229 | 100% |
| *Pseudomonas aeruginosa* ATCC 9027 | 100% |
| *Klebsiella pneumoniae* ATCC 10031 | 100% |
| *Proteus vulgaris* ATCC 6380 | 100% |
| *Staphylococcus aureus* ATCC 6538 | 100% |
| *Staphylococcus epidermidis* ATCC 12228 | 100% |
| *Candida albicans* ATCC 10231 | 100% |

TABLE 2

Microbial challenge studies conducted at UNAM

| TEST MICROORGANISM | CONTACT TIME 30 seconds |
|---|---|
| *Escherichia coli* ATCC 11229 | 99.999% |
| *Staphylococcus aureus* ATCC 6538 | 99.999% |
| *Salmonella typhi* CA-C001 | 99.999% |

TABLE 3

Microbial challenge studies conducted at ARj.

| TEST MICROORGANISM | CONTACT TIME 30 seconds |
|---|---|
| *Escherichia coli* ATCC 11229 | 99.999% |
| *Staphylococcus aureus* ATCC 5538 | 99.999% |
| *Pseudomonas aeruginosa* ATCC 15442-2 | 99.999% |
| *Klebsiella pneumoniae* ATCC 10031 | 100% |
| *Candida albicans* ATCC 10231 | 100% |

A second type of challenges were performed at the Universidad Autónoma del Estado de Morelos with microorganisms collected from hospitalized patients and thus said microorganisms had already been in contact with antimicrobial agents and could show resistance (Table 4).

TABLE 4

Studies conducted at the Universidad
Autónoma del Estado de Morelos

| TEST MICROORGANISM | CONTACT TIME 30 seconds |
|---|---|
| Escherichia coli | 99.961% |
| Staphylococcus aureus | 99.999% |
| Shigella flexnieri | 99.999% |
| Enterobacter cloacae | 100% |
| Serratia marcenses | 100% |
| Salmonella typhi | 99.170% |
| Enterobacter faecalis | 99.972% |
| Salmonella enteritidis | 100% |

TABLE 5

Antimicrobial action of Pirfenidone and M-DDO gel.

| Product | Exposition Time | Percentage of reduction of bacteria viability (%) |
|---|---|---|
| M-DDO 0.016% | 30 sec | 99.999 |
| M-DDO 0.016% | 60 sec | 99.999 |
| M-DDO 0.016% | 15 min | 100 |
| Pirfenidone and M-DDO | 30 sec | 98 |
| Pirfenidone and M-DDO | 60 sec | 98.18 |
| Pirfenidone and M-DDO | 15 min | 99.902 |

The result of these challenges with microorganisms isolated from hospitalized patients was a reduction of at least 99.17% of the microbial charge in only 30 second contact with M-DDO.

EXAMPLES

A semi-solid topical composition containing preferably 8 grams of pirfenidone, 0.016 grams of M-DDO, 92 grams of excipient, was prepared for the treatment of patients with various grades of acne affectation; the results of said application are shown hereinafter: A group of 70 patients with moderate to severe acne, were classified depending on severity grade and the number of inflammatory and non inflammatory lesions, the number of papules, pustules, nodes, open or closed comedones, according to the criteria shown in Table 6.

TABLE 6

| Grade* | Description |
|---|---|
| 0 | Clean skin without inflammatory or non-inflammatory lesions |
| 1 | Nearly clean skin; few non-inflammatory lesions and no more than two inflammatory lesions |
| 2 | Medium severity; higher than Grade 1; some non-inflammatory lesions, a few inflammatory lesions (only papules/pustules; without node lesions) |
| 3 | Moderate severity; higher than Grade 2; many non-inflammatory lesions and various inflammatory lesions, but no more than two node lesions |
| 4 | Severe; higher than Grade 3; many inflamatory and non-inflamatory lesions; and a few node lesions |

*Acne classification scale according to the FDA

TABLE 7

Distribution of the test group:

| Grade | Number of Patients | % |
|---|---|---|
| 0 | 0 | 0 |
| 1 | 14 | 20 |
| 2 | 33 | 47.1 |
| 3 | 19 | 27.2 |
| 4 | 4 | 5.7 |
| Total | 70 | 100 |

The number of lesions for each patient was counted according to the grade of the subject. The resulting data are shown in Table 8, where a reduction averaging nearly 50% with regard to inflammatory lesions after 28 days of treatment can be observed.

TABLE 8

| | Number of Inflammatory Lesions Day | | | | |
|---|---|---|---|---|---|
| Grade | Day 0 | 7 days | 14 days | 21 days | 28 days |
| 1 | 8 +/− 2 | 6 +/− 3 | 5 +/− 2 | 3 +/− 2 | 2 +/− 2 |
| 2 | 24 +/− 8 | 19 +/− 8 | 15 +/− 5 | 12 +/− 4 | 10 +/− 4 |
| 3 | 62 +/− 8 | 48 +/− 6 | 42 +/− 7 | 37 +/− 5 | 33 +/− 5 |
| 4 | 120 +/− 15 | 102 +/− 14 | 88 +/− 16 | 76 +/− 13 | 65 +/− 15 |

The results show that the topical composition of the instant invention permits to obtain an efficacious treatment of acne. These results are comparable to the results obtained with other acne conventional treatments. However, the treatment according to the instant invention is clearly better compared to the pre-existing methods.

Table 9. shows an example of semi-solid topical composition.

| COMPONENT | QUANTITY (g) | % |
|---|---|---|
| PIRFENIDONE | 8.0 | 8.0 |
| VISCOSITY AGENT (Carbomer) | 1.0 | 1.0 |
| SOLUBILIZER (Propylene glycol) | 50.0 | 50.0 |
| NON-IONIC SOLUBILIZER (Macrogolglycerol Hydroxystearate) | 13.0 | 13.0 |
| ANTIMICROBIAL, ANTISEPTIC AGENT (Allicin modified: diallyl disulfide oxide) 2% | 0.8 | 0.016 |
| NEUTRALIZING AGENT (Triethanolamine) | 1.0 | 1.0 |
| PURIFIED WATER Q.S. | 100.0 | 26.984 |

Table 10. shows an example of a semi-solid topical composition containing 2% Pirfenidone.

| COMPONENT | QUANTITY (g) | % |
|---|---|---|
| PIRFENIDONE | 2.0 | 2.0 |
| VISCOSITY AGENT (Carbomer) | 1.0 | 1.0 |
| SOLUBILIZER (Propylene glycol) | 12.5 | 50.0 |
| NON-IONIC SOLUBILIZER (Macrogolglycerol Hydroxystearate) | 3.2 | 13.0 |
| ANTIMICROBIAL, ANTISEPTIC AGENT (Allicin modified diallyl disulfide oxide) 2% | 0.8 | 0.016 |
| NEUTRALIZING AGENT (Triethanolamine) | 1.0 | 1.0 |
| PURIFIED WATER Q.S. | 100.0 | 32.984 |

Table 11. shows an example of a semi-solid topical composition containing 4% Pirfenidone.

| COMPONENT | QUANTITY (g) | % |
|---|---|---|
| PIRFENIDONE | 4.0 | 4.0 |
| VISCOSITY AGENT (Carbomer) | 1.0 | 1.0 |
| SOLUBILIZER (Propylene glycol) | 25.0 | 50.0 |
| NON-IONIC SOLUBILIZER (Macrogol-glycerol Hydroxystearate) | 6.4 | 13.0 |
| ANTIMICROBIAL, ANTISEPTIC AGENT (Allicin modified diallyl disulfide oxide) 2% | 0.8 | 0.016 |
| NEUTRALIZING AGENT (Triethanolamine) | 1.0 | 1.0 |
| PURIFIED WATER Q.S. | 100.0 | 30.984 |

Table 12. shows an example of a semi-solid topical composition containing 6% Pirfenidone.

| COMPONENT | QUANTITY (g) | % |
|---|---|---|
| PIRFENIDONE | 6.0 | 6.0 |
| VISCOSITY AGENT (Carbomer) | 1.0 | 1.0 |
| SOLUBILIZER (Propylene glycol) | 50.0 | 50.0 |
| NON-IONIC SOLUBILIZER (Macrogol-glycerol Hydroxystearate) | 13.0 | 13.0 |
| ANTIMICROBIAL, ANTISEPTIC AGENT (Allicin modified diallyl disulfide oxide) 2% | 0.8 | 0.016 |
| NEUTRALIZING AGENT (Triethanolamine) | 1.0 | 1.0 |
| PURIFIED WATER Q.S. | 100.0 | 28.984 |

Table 13. shows an example of a semi-solid topical composition containing 10% Pirfenidone.

| COMPONENT | QUANTITY (g) | % |
|---|---|---|
| PIRFENIDONE | 10.0 | 10.0 |
| VISCOSITY AGENT (Carbomer) | 1.0 | 1.0 |
| SOLUBILIZER (Propylene glycol) | 50.0 | 50.0 |
| NON-IONIC SOLUBILIZER (Macrogol-glycerol Hydroxystearate) | 13.0 | 13.0 |
| ANTIMICROBIAL, ANTISEPTIC AGENT (Allicin modified diallyl disulfide oxide) 2% | 0.8 | 0.016 |
| NEUTRALIZING AGENT (Triethanolamine) | 1.0 | 1.0 |
| PURIFIED WATER Q.S. | 100.0 | 24.984 |

These compositions are illustrative but not limitative examples of the scope of the instant invention.

Figure 3:
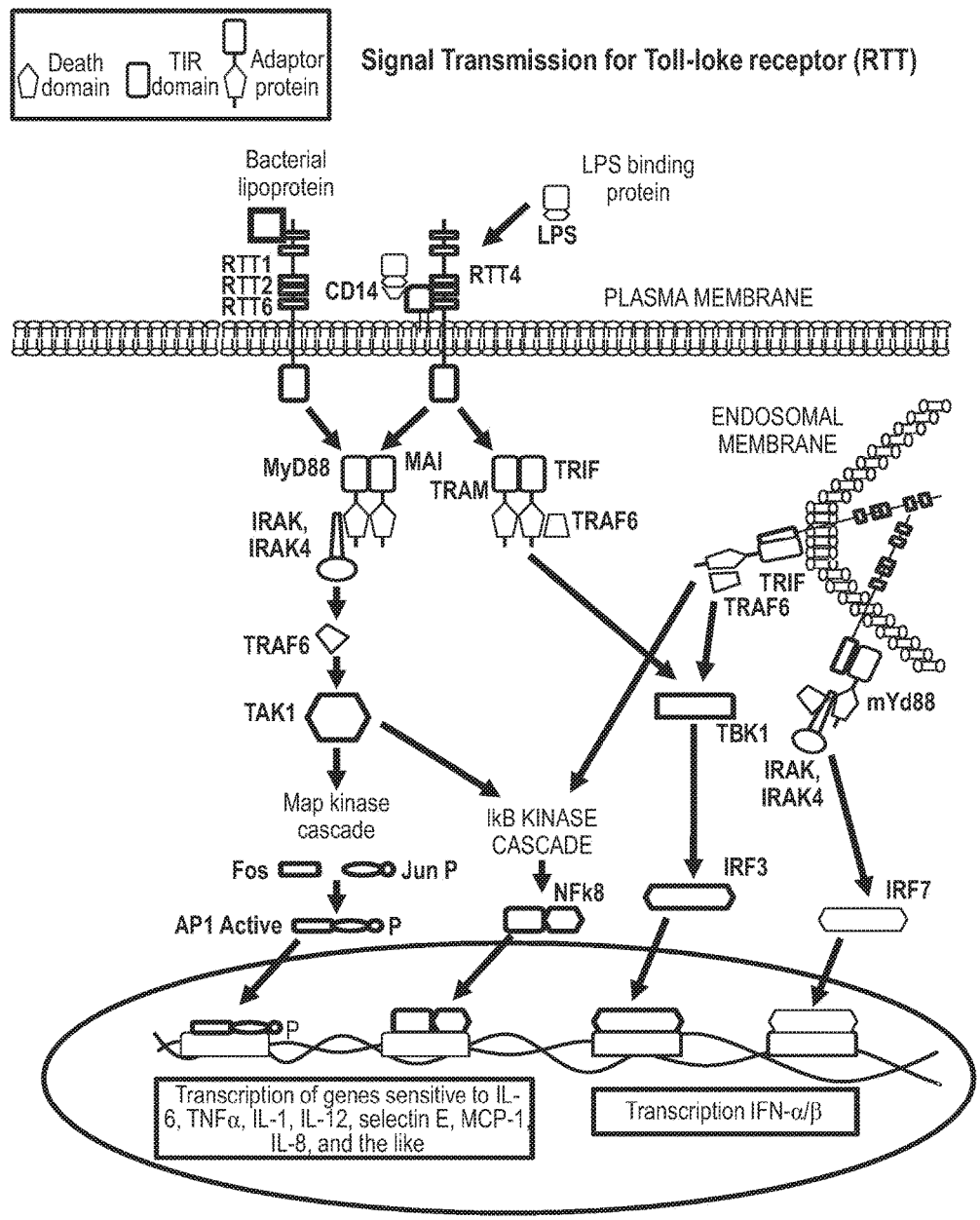
FIG. 3 shows the signal transmission system, at cellular level, intervening in acne and that finally triggers the inflammatory process.
Figure 4:
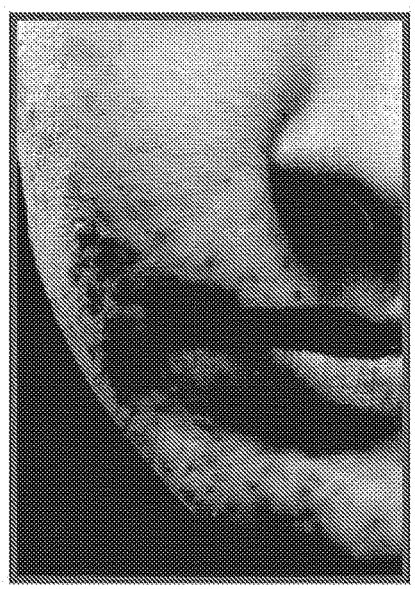
FIGS. 4-15 clearly show the therapeutic effects of the semi-solid topical composition of pirfenidone containing M-DDO for eliminating or preventing acne in 12 patients with different acne types.
Figure 4:
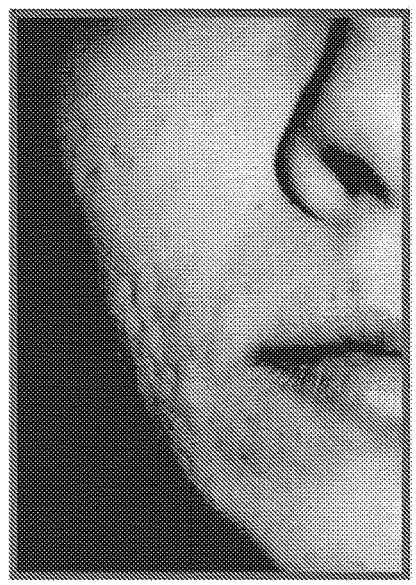
Figure 5:
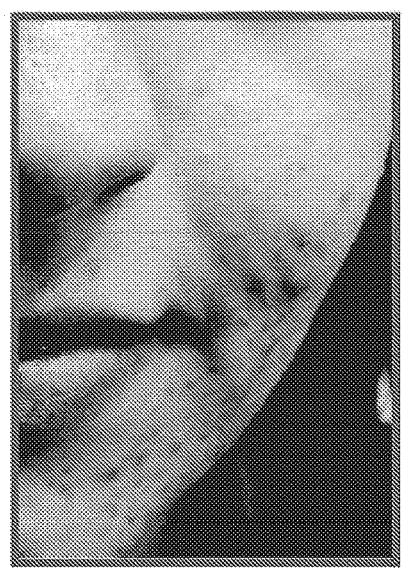
Figure 5:
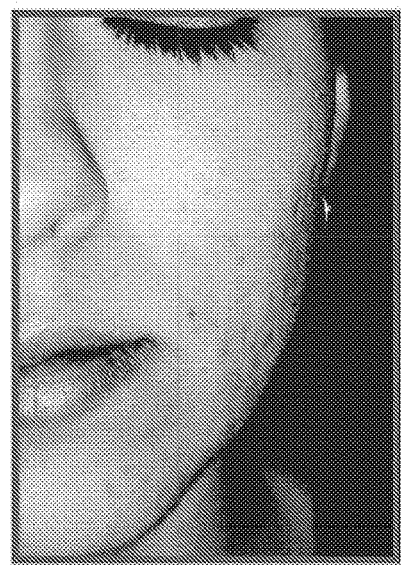
Figure 6:
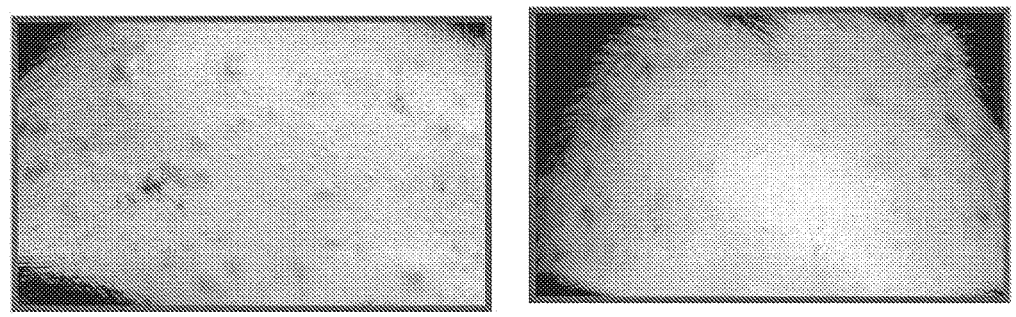
Figure 7:
Figure 7:
Figure 8:
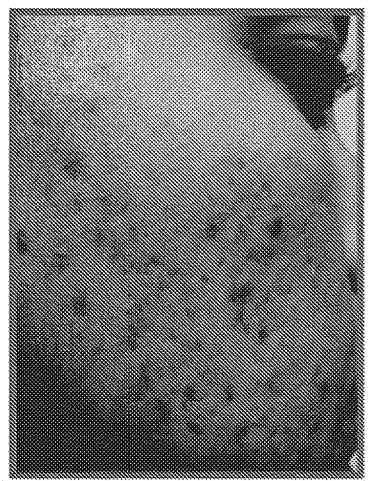
Figure 8:
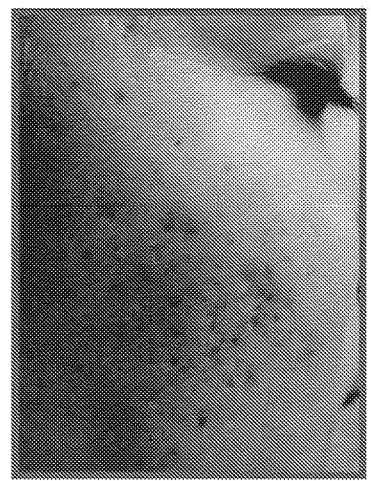
Figure 9:
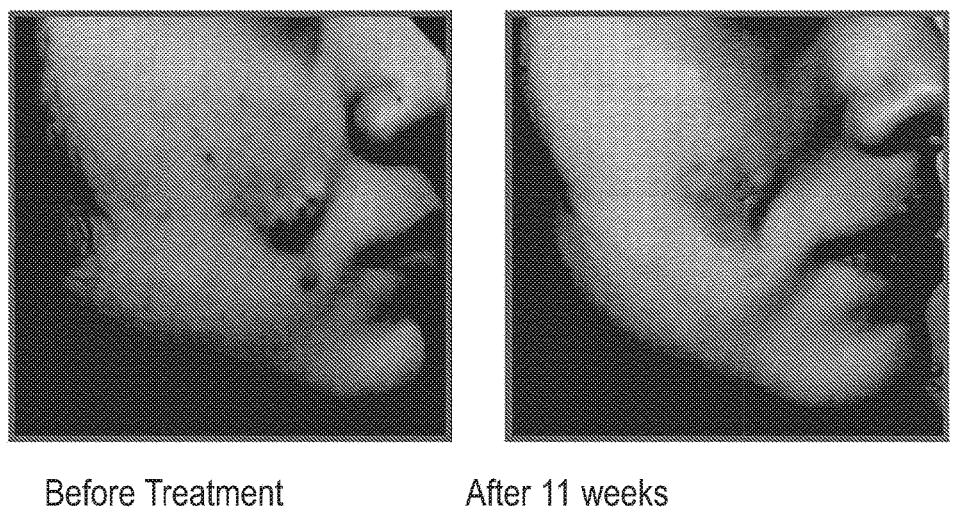
Figure 10:
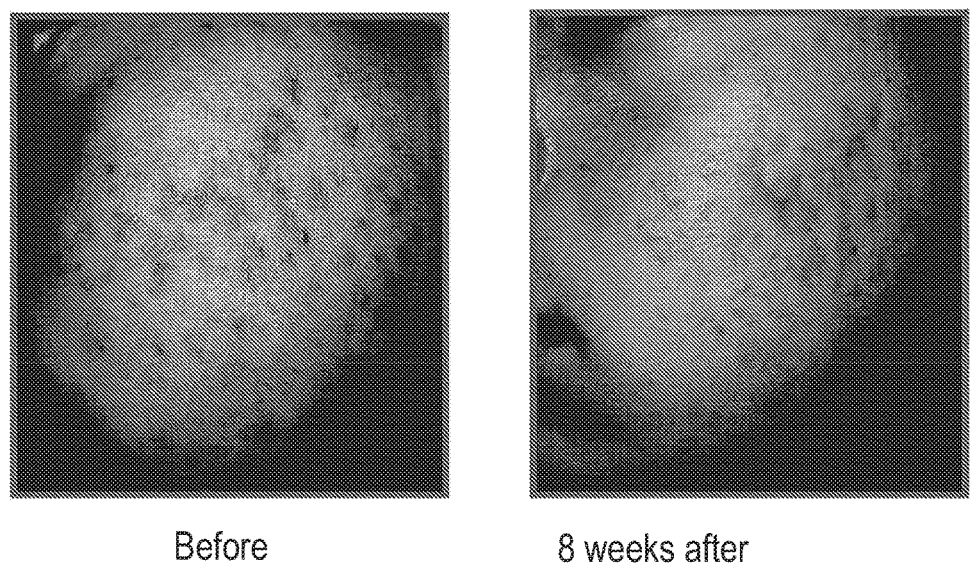
Figure 11:
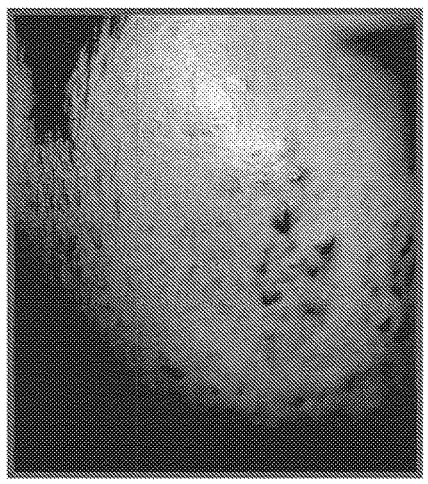
Figure 11:
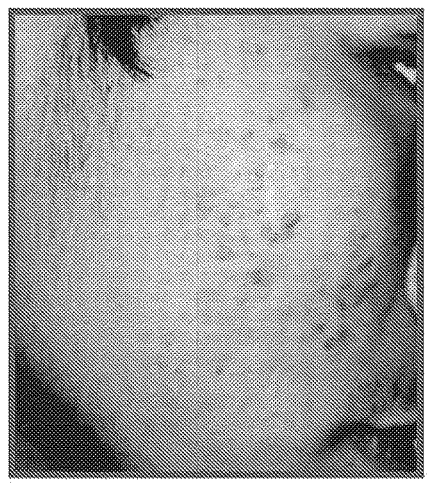
Figure 12:
Figure 12:
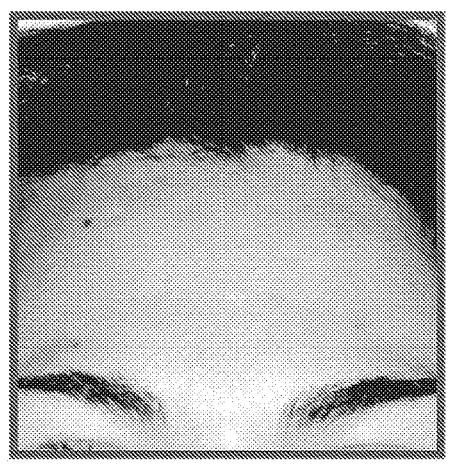
Figure 13:
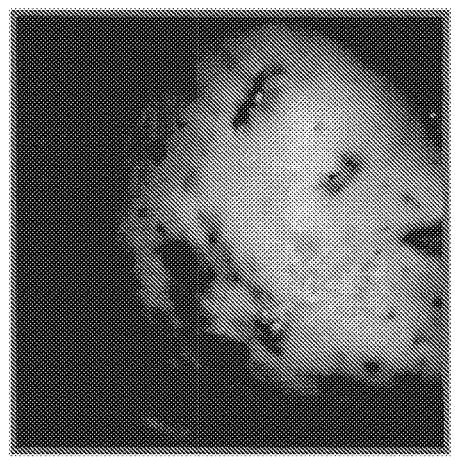
Figure 13:
Figure 14:
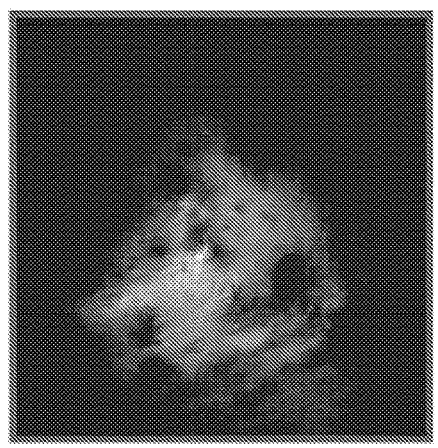
Figure 14:
Figure 15:
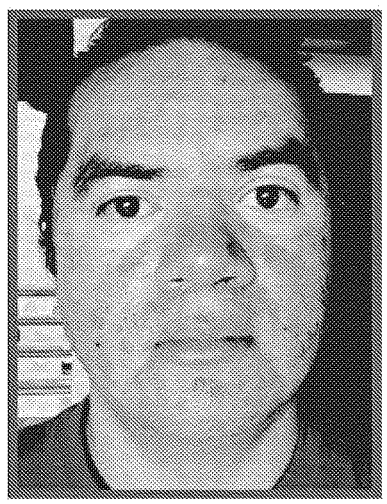
Figure 15:
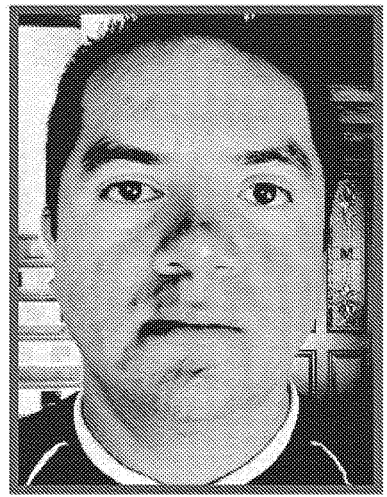

Table 14 shows the definitions of the "acronyms" indicated in FIG. 3.

TABLE 14

| | |
|---|---|
| RTT1 | Toll-like Receptor 1 |
| RTT2 | Toll-like Receptor 2 |
| RTT4 | Toll-like Receptor 4 |
| RTT6 | Toll-like Receptor 6 |
| MD-2 | Molecule that associates with the extra cellular portion of TLR4 |
| CD14 | CD14 Receptor |
| Myd88 | Myeloid Differentiation Factor 88 |
| IRAK | IL-1 Receptor Associated Kinase |
| TRAF-6 | TNF receptor associated factor 6 |
| MAPK | Mitosis activated protein kinase |
| NF-kβ | Nuclear Factor Kappa-Beta |
| LPS | Lipopolysaccharide |
| TIR | Toll/interleukin receptor |
| AP-1 | Activator protein 1 |
| IRF 3 | Interferon regulatory protein 3 |
| IRF7 | Interferon regulatory protein 7 |
| TAK1 | Activated Kinase 1 |
| TRIF | Toll Factor/IL-1R |
| TBK1 | TANK binding kinase 1 |
| TRAM | TRIF related adaptor molecule |
| IFN | Interferon |

The invention claimed is:

1. A semi-solid topical composition for eliminating or reducing skin acne occurrence, comprising 2%, 4%, 6%, 8% or 10% in weight of pirfenidone, 0.016% in weight of {[1,2-diallyl-1-(5-methyl-tetrahydro-2H-pyran-2-yloxy)disulfonium]+6-[(benzyl, methyl, octylammonium)(hydroxymethylamin)(methylamin)]-tetrahydro-2H-pyran-3-oxy]}chloride (M-DDO), and 91.984% in weight of a gelling agent and other excipients or additives.

2. The semi-solid topical composition according to claim 1, comprising 8% in weight of the pirfenidone, 0.016% in weight of the M-DDO and 91.984% in weight of the gelling agent and other excipients or additives.

3. The semi-solid topical composition according to claim 1, wherein the gelling agent is selected from the group consisting of methylcellulose, hydroxypropylcellulose, sodium carboxymethylcellulose, polyvinyl alcohol, polyvinylpirrolidone, carboxyvinyl polymers, carbomer and acrylic polymers.

4. The semi-solid topical composition according to claim 3, wherein the gelling agent is carbomer.

5. The semi-solid topical composition according to claim 1, wherein the excipients or additives are selected from the group consisting of propylene glycol as a solubilizer, macrogol-glycerol hydroxystearate as a non-ionic solubilizer and triethanolamine as a neutralizing agent.

6. The semi-solid topical composition according to claim 1, wherein said composition is in gel, cream or ointment form.

7. The semi-solid topical composition according to claim 1, having a pH of 5 to 6.4.

8. A method of eliminating or reducing acne, comprising administering a semi-solid topical composition according to claim 1 to the skin of a person in need thereof.

9. A method for eliminating or reducing chronic inflammation caused by acne, reducing skin redness, reversing existing outbreaks, regenerating skin damage caused by acne and/or removing post-acne scars, the method comprising administering a semi-solid topical composition according to claim 1 to the skin of a person in need thereof.

* * * * *